United States Patent [19]

Marsoner et al.

[11] Patent Number: 4,917,864

[45] Date of Patent: Apr. 17, 1990

[54] DEVICE FOR FEEDING AN ANALYZING APPARATUS

[75] Inventors: Hermann Marsoner, Steinberg; Erich Kleinhappl, Graz, both of Austria

[73] Assignee: AVL AG, Austria

[21] Appl. No.: 192,615

[22] Filed: May 11, 1988

[30] Foreign Application Priority Data

May 12, 1987 [AT] Austria ............................ A1204/87

[51] Int. Cl.$^4$ .......................................... G01N 35/00
[52] U.S. Cl. ......................................... 422/63; 422/68.1; 422/83; 422/82.01; 422/82.05; 73/863.73
[58] Field of Search ................................ 422/63–68, 422/81, 83, 50; 141/130, 141, 163; 73/863.71, 863.72, 863.73, 864.83, 864.84; 403/328

[56] References Cited

U.S. PATENT DOCUMENTS

| 2,549,397 | 4/1951 | Sparks | 403/328 |
| 2,851,295 | 9/1958 | Chaffee | 403/328 |
| 3,030,192 | 4/1962 | Schneider, Jr. | 422/81 |
| 3,386,472 | 6/1968 | Szonntagh | 73/863.73 |
| 3,475,950 | 11/1969 | Ferrin | 73/863.73 |
| 3,570,314 | 3/1971 | Wagner | 422/64 |
| 3,682,506 | 8/1972 | Bruyere et al. | 285/315 |
| 3,901,084 | 8/1975 | Brailsford | 141/130 |
| 4,475,411 | 10/1984 | Wellerfors | 422/64 |
| 4,737,342 | 4/1988 | Herrmann et al. | 422/64 |

FOREIGN PATENT DOCUMENTS 0112324  6/1984  European Pat. Off. .
3104617  1/1982  Fed. Rep. of Germany .

Primary Examiner—Michael S. Marcus
Assistant Examiner—D. John Griffith, Jr.
Attorney, Agent, or Firm—Watson, Cole, Grindle and Watson

[57] ABSTRACT

In conventional devices for feeding an analyzing apparatus with different media, comprising a feeder unit with fittings for the media to be introduced, the individual media travel different paths between the input opening and the measuring chambers, which will result in different conditions of measurement for calibrating media and sample media. The invention eliminates this drawback by providing the feeder unit 1 with input elements 6, by placing the sample input opening 4 on a supporting piece 3 which may be moved by a control unit 17, and by providing that each input element 6 may be brought into sealing contact with the sample input opening 4 subsequent to a rotatory motion of the supporting piece 3.

10 Claims, 2 Drawing Sheets

DEVICE FOR FEEDING AN ANALYZING APPARATUS

BACKGROUND OF THE INVENTION

The invention relates to a device for alternatively feeding an analyzing apparatus with liquid or gaseous test-, reference- or cleansing media, comprising a sample input opening and a feeder unit with fittings for the media to be introduced.

DESCRIPTION OF THE PRIOR ART

Chemical analyses utilizing the kind of test equipment for which the above feeding device is designed, are preferably performed by introducing the sample via the above sample feeding device into measuring chambers, where it is brought into contact with measuring sensors. As a result of the interaction of the sample and these sensors an electric signal will eventually be generated, in general by means of physical or chemical interactions, which is functionally dependent on the concentration of the substance to be determined in the sample.

Devices of this type are known, for instance, for carrying out blood gas analyses or electrolyte analyses with the use of electrochemical or optochemical sensors. Examples of the substance concentrations measured include the pH value of a blood sample, the partial pressure of oxygen in molecular solution, the partial pressure of $CO_2$ in molecular solution, and, possibly a number of ions, enzymes and non-electrolytes contained in the solution, such as glucose, etc,- parameters which in their entirety provide information on the state of the sample and, as such, on the constitution of the test person.

The analyzing apparatus should therefore be provided with a device permitting the feeding of all kinds of sample materials into the measuring chambers, and it should also be possible to introduce calibrating liquids, calibrating gases, cleansing solutions, test solutions, i.e., media of a liquid or gaseous type, in a simple manner, with the samples being fed into the input opening from their conventional sample containers, such as syringes or capillary glass tubes. Depending on the desired or specified method of operation and optimized sample manipulation, the sample is injected into the input opening from a syringe, or it is sucked into the sample input opening from capillary tubes of variable length and diameter by means of a pumping device of the analyzing apparatus. If gaseous samples or calibrating media are to be introduced, great care should be taken to avoid the build-up of any dynamic pressure anywhere in the sample path, since this might falsify the absolute value of the respective partial pressure of the gas.

A device of the above type, for example for feeding selected media into an electrochemical test apparatus, is described in European patent No. 0 112 324. This device is provided with a stationary feeder unit carrying fittings for the feeding of calibrating and reference media, and a sealed piece of pipe positioned in a bore, which is movable relative to the feeder unit. On its end facing away from the measuring chamber this piece of pipe has a fitting for the sample as well as one or more bores along its circumference, which may be aligned with one or more of the above fittings for the calibrating and reference media by means of a relative motion between the piece of pipe and the feeder unit, which is controlled by a stepping motor.

Although this device has proved successful, it suffers from the drawback that the paths to the measuring chamber taken by the sample medium and any reference or calibrating media will differ—even if only slightly, where interactions with the materials of the paths and differences in temperature and pressure may occur. This means that the sample-, reference- and calibrating media are not subject to identical conditions, which may result in considerable errors of measurement.

SUMMARY OF THE INVENTION

It is an object of the present invention to avoid the disadvantages of the previous devices and to propose a feeding device offering identical conditions of measuring for all input media and minimizing the wear of fittings and sealings caused by the relative movement between feeder unit and sample input opening.

In the present invention this object is achieved by providing the feeder unit with input elements and by locating the sample input opening on a supporting piece which may be moved by a control unit, and by providing that each input element can be brought into sealing contact with the sample input opening subsequent to a rotatory motion of the supporting piece. All input media are fed from the individual input elements into the input opening moving along with the supporting piece, thus taking the same path between sample input opening and the individual measuring chambers inside the analyzing apparatus. For sample input the supporting piece is moved until the sample input opening is easily accessible from outside and may be connected with a sample container, for instance a syringe or a capillary tube. The input elements can be made stationary and the sample input opening can be brought into a coaxial position relative to the input element by a rotatory motion, such that upon further motion of the input opening the latter is brought into sealing contact with the input element. With this design the wear of the input and output elements can be kept at a minimum.

If a slight axial shift of the input elements is tolerated, a further development of the invention may provide that guide elements carrying the input elements be placed along the inner circumference of the feeder unit, and that the supporting piece of the sample input opening be designed rotationally symmetric, such that a rotatory motion of the supporting piece effected by the control unit will serve to position an input element above the sample input opening and the input element can be inserted into the sample input opening by an axial displacement of the guide element parallel to the axis of the sample input opening. The axial displacement of the guide elements, and thus the input elements, does not exceed a few millimeters, which can easily be accommodated by elastic fittings without noticeably reducing their service life.

In order to avoid the torsional motion of the sample passage induced by a rotatory motion of the supporting piece, a further development of the invention provides that a sample passage communicating with the sample input opening be connected by a coupling to the inlet stub of a unit containing measuring chambers, in such a way as to be axially rotatable. This variant, unlike the known designs, will require not more than one coupling and sealing element in the sample path, which must seal tightly against a rotatory motion of the sample passage relative to the analyzing apparatus.

According to the present invention a particularly simple design of the feeding device is obtained if the axis of the sample input opening and that of the supporting piece are at right angles, and if the sample passage leaves the supporting piece in the area of its axis, and if the feeder unit is configured as a cylindrical housing enclosing the supporting piece at least partially. The cylindrical housing may be pot-shaped, with the motor being located on the outside of its bottom, and a shaft being mounted on the inside, at a position concentric to the axis of the cylinder, which shaft will act as a bearing for the supporting piece of the sample input opening and the sample passage.

The sequence of motions necessary for introducing the individual input elements into the sample input opening is realized in another variant of the invention, by providing the control unit with a plate cam driven from a motor, possibly via a gear, which plate cam is concentric to the supporting piece and is cooperating with the guide elements via its circumference acting as a shifting gate in order to achieve an axial shifting of the input elements, and, further, by providing the plate cam with a driving pin running in a groove on the supporting piece bounded by stops, such that the supporting piece will be rotated together with the plate cam as soon as the driving pin is resting against one of the stops. In this variant of the invention both relative motions, i.e., the axial shift of the input elements as well as the rotatory motion of the supporting piece, are achieved by a single motor. As soon as the supporting piece—which is driven by the driving pin of the plate cam—has reached the desired input position, the direction of rotation of the plate cam is reversed, the supporting piece being at a standstill for as long as the driving pin is moving along the groove of the supporting piece. During the time of standstill of the supporting piece, the respective input element is lowered into the sample input opening. If the rotation continues in the same direction, the input element is lifted by means of the shifting gate before the driving pin comes to rest against the second stop bounding the groove, whereupon the supporting piece may be further rotated in the respective direction. It is also possible, of course, to fasten the driving pin on the supporting piece and to provide the plate cam with a groove.

Another variant of the invention provides that the guide elements contain lifting magnets for the axial displacement of the input elements, which may be activated by the control unit, thus providing a separate drive for each of the two relative motions.

In all of the above variants of the invention the guide elements may be pressed against the circumference of the plate cam acting as a shifting gate by means of springs, which are preferably supported by the cylindrical housing of the feeder unit.

According to a preferred variant of the invention the supporting piece carries a ring-shaped part additionally supporting the guide elements, with a recess into which that guide element may be lowered whose input element is positioned above the sample input opening. By supporting the guide elements along a ring-shaped part of the supporting piece, which part has a recess whose position on the circumference corresponds with that of the sample input opening, the guide element, and thus the input elements, may be lowered only if the respective input element is positioned above the sample input opening. This will afford a certain protection to the device by helping avoid errors in control.

Advantages for sample input by means of a syringe or dropper are obtained by providing the cylindrical housing with an opening in its wall, and by configuring the rotationally symmetric supporting piece as a sphere, and by letting the sample input opening rise above the plane defined by the opening in the cylindrical wall in the sample input position. The geometrical shape of the supporting piece could also be non-spherical, of course, as long as it is guaranteed that the sample input opening will rise above the opening in the housing or any other cover used.

According to another favorable variant of the invention the supporting piece may be fixed in axial direction on a shaft by means of a rapid action coupling, preferably a spring-loaded ball placed in a bore of the shaft. This will permit the supporting piece carrying the sample input opening and the sample passage, to be easily removed from the shaft and taken out of the apparatus for cleaning purposes or a replacement of parts.

A further variant of the invention may finally provide that one of the guide elements carries a conventional cleaning device for the sample input opening. Such a device is described, for instance, in German laid open No. 31 04 617.

BRIEF DECRIPTION OF THE DRAWINGS

The invention will now be illustrated, by way of examples, with reference to the accompanying drawings, in which FIGS. 1 and 2 present sectional views of a device as described by the invention, and FIGS. 3 and 4 present other variants, the sections corresponding to that of FIG. 1.

DETAILED DESCRIPTION OF THE PREFERRED EMBODIMENTS

Figure 1:
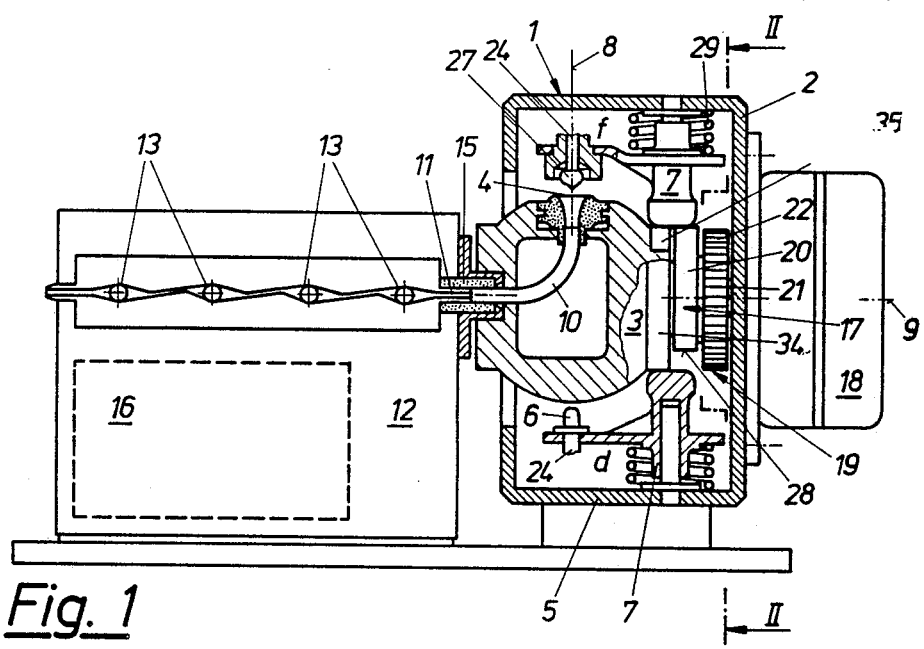
Figure 2:
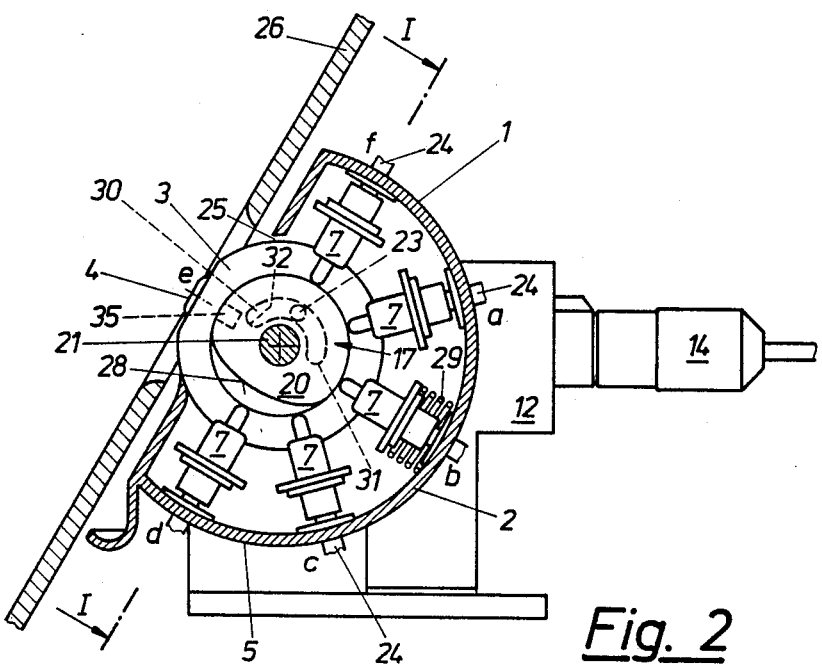

In the device shown in FIGS. 1 and 2 the feeder unit 1 is constituted by an essentially cylindrical housing 2 which encloses the supporting piece 3 of the sample input opening 4 in parts. On the wall 5 of the housing 2 the input elements 6 are mounted by means of guide elements 7 permitting an axial shift parallel to the axis 8 of the sample input opening 4. The supporting piece 3, which is rotatably mounted in the housing 2 and is of essentially spherical shape, supports the sample input opening 4 whose axis 8 is normal to the axis 9 of the supporting piece 3; the sample input opening 4 is made of elastic material and is shaped like a funnel opening towards the input elements 6. In the area of the axis 9 a sample passage 10, which may be attached to the sample input opening 4, runs from the supporting piece 3 straight to the inlet stub 11 of a unit 12 with measuring chambers 13 arranged in line and measuring electrodes 14. The sample passage 10 and the inlet stub 11 are rotatably connected by means of a coupling 15, for instance made of soft plastic material. The unit 12 contains a unit 16 acting as a temperature control of the measuring chambers 13.

The control unit 17 effecting the geometric displacement of the supporting piece 3 comprises a motor 18 as well as a gear 19 and a plate cam 20, which—together with the supporting piece 3—are supported on a shaft 21 attached to the housing 2. The plate cam 20 is rigidly connected with the toothed wheel 22 of the gear 19, driving the supporting piece 3 by means of a driving pin 23 to be discussed in greater detail below.

In the feed positions a–d the cylindrical housing 2 is provided with input elements 6 for liquid or gaseous buffer-, reference- or cleansing media, which are introduced from their containers (not shown here) via fittings 24. In the sample input position the sample input opening 4 is situated in e. As is shown in FIG. 2 the sample input opening 4 rises above the plane defined by the opening 25 in the wall 5 of the housing 2 and the cover 26 parallel to this plane, which will facilitate sample input by means of a dropper, a syringe or similar such device. As compared to FIG. 1, the supporting piece 3 has been turned by 90 degrees in FIG. 2.

In the cleaning position f a cleaning device 27 may be introduced into the sample input opening 4 via the corresponding guide element 7, and a cleansing solution may be added at the same time.

Lowering of the input element 6 above the sample input opening 4 is effected by the circumference of the plate cam 20 acting as a shifting gate 28, during which process the guide element 7 is pressed against the gate 28 by a spring 29 supported by the wall 5 of the housing 2.

Shifting the input device from one input position to the next is effected as following.

Upon movement of the plate cam 20 the guide element 7 is lifted by the shifting gate 28. The driving pin 23 attached to the plate cam 20 is guided in a groove 30 of the supporting piece 3, which is shaped as a circular arc, until it is arrested by one of the stops 31, 32 bounding the groove 30. After this the supporting piece 3 will rotate together with the plate cam 20 until the next input position is reached. Subsequent to this the direction of rotation of the motor 18 and thus the plate cam 20 is reversed, the supporting piece 3 coming to a standstill, and the next guide element 7 is lowered by the shifting gate 28 rotating in the opposite direction.

Figure 3:
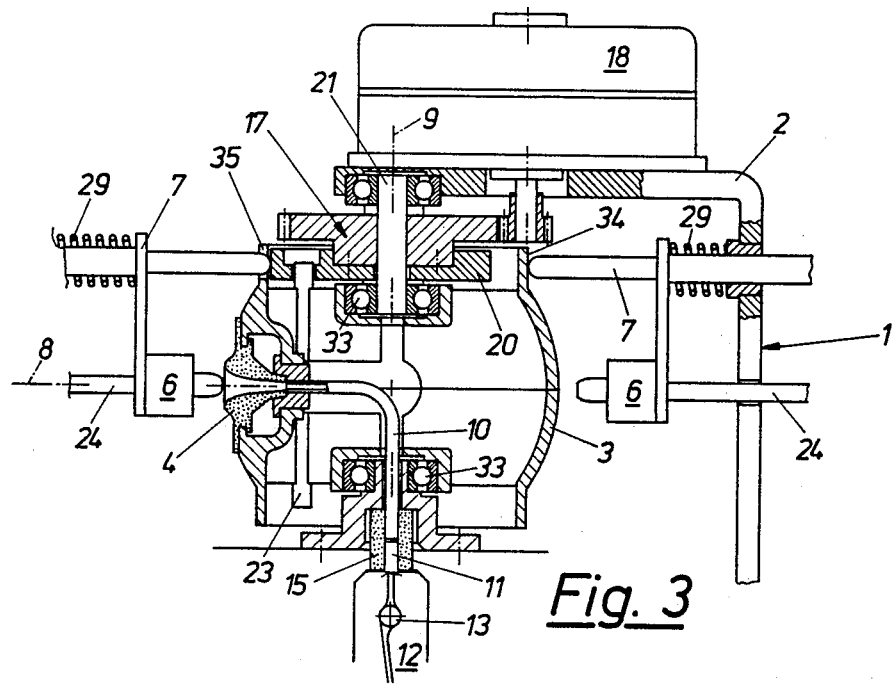

In the variant according to FIG. 3 the input elements 6, whose number need not be limited, are guided—again by means of guide elements 7—along a shifting gate and a ring-shaped part 34 of the supporting piece 3, such that in positions in which they are not directly aligned with the sample input opening 4, the input elements 6 are lifted to the extent that the spherical supporting piece 3, together with the sample input opening 4 and the sample passage 10 leading to the measuring chambers, can move freely around its axis 9. Via the control unit 17 a given input position of the input elements 6 may be selected such that one of the input elements will assume a coaxial position relative to the sample input opening 4. The supporting piece 3, which may be moulded from rigid plastic, for example, is supported on two roller bearings 33 in this instance. The driving pin is fastened in the supporting piece 3 in this case, sliding in a groove in the plate cam 20.

Figure 4:
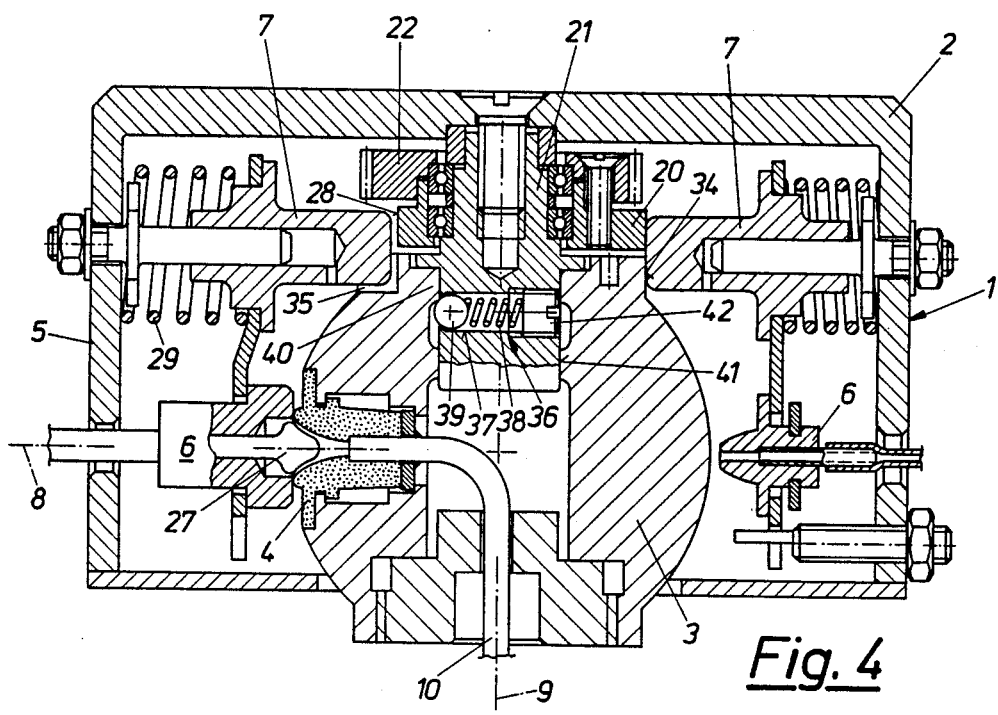

In the variant according to FIG. 4 all parts corresponding to those of the previous variants have the same reference numbers as above. It is shown clearly that the supporting piece 3 carries a ring-shaped part 34 supporting the guide elements 7 in addition to the plate cam 20. The ring-shaped part 34 has a recess 35 for the respective guide element 7 whose input element 6 is positioned above the sample input opening 4. By rotating the shifting gate 28 the input element 6 may be lowered into the sample input opening 4. The supporting piece 3 configured as a rotating part is supported by the shaft 21 on the side of the motor only, and is secured in axial direction by a rapid action coupling 36 consisting of a ball 39 which is loaded by a spring 38 and is located in a bore 37 of the shaft 21; in the assembled state of the coupling the ball 39 presses against a ring-shaped shoulder 40 of the bore 41 in the supporting piece 3. On the side of the coupling 36 opposite of the ball 39 the bore 37 is closed by a worm screw 42. In this way the supporting piece 3 may easily be pulled off the shaft 21 in axial direction, and removed from the input device.

We claim:

1. A device for alternatively feeding an analyzing apparatus with liquid or gaseous sample, reference or cleansing media, comprising a sample receiving means defining a sample input opening on a circumferential surface of a supporting piece, a feeder unit disposed about said sample receiving means with fittings for said liquid or gaseous sample, reference or cleansing media to be introduced, wherein said feeder unit has an inner circumference which is provided with guide elements carrying insertable input elements and wherein said sample input opening located on said supporting piece is rotationally symmetric with said feeder unit, and a control unit rotating said supporting piece to position one of said input elements in alignment with and radially outward from said sample input opening wherein said control unit during alignment inserts said input element sealingly into said sample input opening by an axial displacement of said guide element parallel to said sample input opening.

2. A device according to claim 1, wherein said guide elements are provided with lifting magnets for effecting said axial displacement of said input elements, and said lifting magnets are activated by said control unit.

3. A device according to claim 1, wherein one of said guide elements is provided with a conventional cleaning device for said sample input opening.

4. A device according to claim 1, wherein said control unit is provided with a plate cam driven from a motor, said plate cam comprising a circumference acting as a shifting gate, wherein said plate cam is concentric to said supporting piece and is cooperating with said guide elements via said shifting gate in order to achieve an axial shifting of said input elements, and wherein said plate cam is provided with a driving pin running in a groove on said supporting piece, each groove is bounded by stops, and wherein said supporting piece is rotated together with said plate cam as soon as said driving pin is resting against one of said stops.

5. A device according to claim 4, wherein said guide elements are pressed against said circumference of said plate cam acting as a shifting gate by means of springs, which are supported by said cylindrical housing of said feeder unit.

6. A device according to claim 4, wherein said supporting piece adjacent to said plate cam comprises a ring-shaped part additionally supporting said guide elements, and wherein said ring-shaped part has a recess for receiving one of said guide elements which is lowered to insert one of said input elements into said sample input opening.

7. A device according to claim 1, wherein said supporting piece has a sample passage communicating at a first end with said sample input opening and is connected at a second end to an inlet stub of a unit containing measuring chambers by means of an axially rotatable coupling.

8. A device according to claim 7, wherein the longitudinal axis of said sample input opening and the axis of rotation of said supporting piece are at right angles, and said second end of said sample passage leaves said supporting piece coaxial to said axis of rotation of said supporting piece, and wherein said feeder unit is configured as a cylindrical housing enclosing said supporting piece at least partially.

9. A device according to claim 8, wherein said control unit is provided with a plate cam driven from a motor, said plate cam comprising a circumference acting as a shifting gate, wherein said plate cam is concentric to said supporting piece and is cooperating with said guide elements via said shifting gate in order to achieve an axial shifting of said input elements, and wherein said plate cam is provided with a driving pin running in a groove on said supporting piece, which groove is bounded by stops, and wherein said supporting piece is rotated together with said plate cam as soon as said driving pin is resting against one of said stops.

10. A device according to claim 8, wherein said cylindrical housing has an opening, and wherein said rotationally symmetric supporting piece is configured as a sphere, and wherein said sample input opening will rise above a plane defined by said opening in said cylindrical housing in a supplemental sample input position.

* * * * *

UNITED STATES PATENT AND TRADEMARK OFFICE
CERTIFICATE OF CORRECTION

PATENT NO.  : 4,917,864
DATED       : April 17, 1990
INVENTOR(S) : Hermann MARSONER et al.

It is certified that error appears in the above-identified patent and that said Letters Patent is hereby corrected as shown below:

On the title page, column 1, item (73), change
    "Austria" to read --Schaffhausen, Switzerland--.

Signed and Sealed this

Twenty-fifth Day of August, 1992

*Attest:*

DOUGLAS B. COMER

*Attesting Officer*   Acting Commissioner of Patents and Trademarks